United States Patent

Maywald et al.

(10) Patent No.: US 10,538,493 B2
(45) Date of Patent: Jan. 21, 2020

(54) PROCESS FOR THE PURIFICATION OF 1-(4-CHLOROPHENYL)PYRAZOL-3-OL

(71) Applicant: BASF SE, Ludwigshafen am Rhein (DE)

(72) Inventors: Volker Maywald, Ludwigshafen (DE); Roland Goetz, Ludwigshafen (DE); Daniel Saelinger, Ludwigshafen (DE); Timo Frassetto, Ludwigshafen (DE); Stefan Gropp, Ludwigshafen (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 16/348,610

(22) PCT Filed: Nov. 9, 2017

(86) PCT No.: PCT/EP2017/078680
§ 371 (c)(1),
(2) Date: May 9, 2019

(87) PCT Pub. No.: WO2018/091338
PCT Pub. Date: May 24, 2018

(65) Prior Publication Data
US 2019/0270710 A1    Sep. 5, 2019

(30) Foreign Application Priority Data
Nov. 17, 2016 (EP) .................................. 16199237

(51) Int. Cl.
C07D 231/22    (2006.01)
(52) U.S. Cl.
CPC ........ C07D 231/22 (2013.01); C07B 2200/13 (2013.01)
(58) Field of Classification Search
CPC .................... C07D 231/22; C07B 2200/13

USPC ...................................................... 548/371.1
See application file for complete search history.

(56) References Cited

U.S. PATENT DOCUMENTS 5,922,886 A    7/1999  Konig et al.
6,040,458 A    3/2000  Vogelbacher et al.
9,624,177 B2   4/2017  Nakae et al.

FOREIGN PATENT DOCUMENTS

| DE | 19652516 A1 | 6/1998 |
| EP | 3112350 B1 | 4/2018 |
| WO | 13162072 A1 | 10/2013 |
| WO | 14051165 A1 | 4/2014 |
| WO | 15129591 A1 | 9/2015 |
| WO | 15189080 A1 | 12/2015 |
| WO | 16071243 A1 | 5/2016 |
| WO | 16113741 A1 | 7/2016 |
| WO | 16180833 A1 | 11/2016 |
| WO | 16202807 A1 | 12/2016 |
| WO | 17102905 A1 | 6/2017 |
| WO | 17133942 A1 | 8/2017 |
| WO | 17144336 A1 | 8/2017 |
| WO | 17144337 A1 | 8/2017 |
| WO | 17215928 A1 | 12/2017 |
| WO | 17215929 A1 | 12/2017 |
| WO | 18035685 A1 | 3/2018 |
| WO | 18050518 A1 | 3/2018 |

OTHER PUBLICATIONS

Ren et al., "1-(4-Chlorophenyl)-1H-pyrazol-3-ol," Acta Cryst., vol. E66, (2010), pp. o186-sup-5.
Search Report, issued in EP Application No. 16199237.5, dated May 12, 2017.
International Search Report, issued in PCT/EP2017/078680, dated Jan. 24, 2018.
International Preliminary Report on Patentability, issued in PCT/EP2017/078680, dated May 21, 2019.

Primary Examiner — Kristin A Vajda
(74) Attorney, Agent, or Firm — Brinks Gilson & Lione

(57) ABSTRACT

The present invention relates to a process to produce highly purified crystalline 1-(4-chlorophenyl)pyrazol-3-ol (I).

7 Claims, No Drawings

PROCESS FOR THE PURIFICATION OF 1-(4-CHLOROPHENYL)PYRAZOL-3-OL

This application is a National Stage application of International Application No. PCT/EP2017/078680 filed Nov. 9, 2017. This application also claims priority under 35 U.S.C. § 119 to European Patent Application No. 16199237.5, filed Nov. 17, 2016.

The present invention relates to a process for preparing crystalline 1-(4-chlorophenyl)pyrazol-3-ol a) comprising contacting a metal 1-(4-chlorophenyl)pyrazol-3-olate in aqueous solution with a solvent, wherein
  i. the solvent is selected from anisole or cyclopentyl methyl ether; and
  ii. the temperature is between 0° C. and the boiling point of the mixture; and
  iii. the pH of the mixture is adjusted to ≤8 using an acid; and
b) removing the aqueous phase; and
c) crystallizing 1-(4-chlorophenyl)pyrazol-3-ol in the solution resulting from step b).

Crystalline 1-(4-chlorophenyl)pyrazol-3-ol is an important intermediate for preparation of commercial pesticides, for example pyraclostrobin or tetrazolinones described in WO 13162072 and WO 14051165.

The most straightforward synthesis approach for 1-(4-chlorophenyl)pyrazol-3-ol starts from the raw materials (4-chlorophenyl)hydrazine and methyl acrylate and occurs via intermediates like 1-(4-chlorophenyl)pyrazolidin-3-one (salt and free acid) followed by an oxidation to a potassium or sodium 1-(4-chlorophenyl)pyrazol-3-olate (see for example DE 19652516 A 1). For the synthesis of the above-mentioned fungicidal active compounds the metal 1-(4-chlorophenyl)pyrazol-3-olates may be either directly used as raw aqueous solutions or as isolated, protonated form 1-(4-chlorophenyl)pyrazol-3-ol). The protonated form 1-(4-chlorophenyl)pyrazol-3-ol is in general purified/isolated from the metal salts by acidification with suitable inorganic or organic acids, precipitation and solid-liquid separation. However, main disadvantage of the last mentioned isolation method is that 1-(4-chlorophenyl)pyrazol-3-ol is obtained here in moderate purity only, being often not sufficient for the use as synthesis intermediate in technical fungicide synthesis, since there are requirements for having as less by-products in end-use products as possible. Thus, there is the need to make highly purified starting materials available on a large technical scale. The required degree of purity is e.g. at least 98%-by weight or higher in the crystalline product.

However, practically, such high degree of purity is only possible to be achieved at large technical scales with crystallization via multiple steps, which leads to considerable yield losses.

Furthermore, 1-(4-chlorophenyl)pyrazol-3-ol exists in various crystal forms (polymorphs). One stable polymorph of 1-(4-chlorophenyl)pyrazol-3-ol (crystal system: monoclinic, space group: P $2_1$/c), hereinafter referred to as polymorph I is described in Acta Crystallographica Section E, Volume 66, Part 1, January 2010, page o186. For specific applications, it may be advantageous to have polymorph I produced without the presence of other polymorphs.

Surprisingly, it has been found that 1-(4-chlorophenyl)pyrazol-3-ol can be produced at a purity of at least 98% by weight in the crystalline product in high yields by a method comprising a) contacting an aqueous solution of a metal 1-(4-chlorophenyl)pyrazol-3-olate with a solvent; wherein
  i. the solvent is selected from anisole or cyclopentyl methyl ether; and
  ii. the temperature is between 0° C. and the boiling point of the mixture; and
  iii. the pH of the solution is adjusted to ≤8; and
b) removing the aqueous phase; and
c) crystallizing 1-(4-chlorophenyl)pyrazol-3-ol in the solution resulting from step b).

Furthermore, surprisingly, it has been found that using the method of the present invention, polymorph I of 1-(4-chlorophenyl)pyrazol-3-ol is obtained without presence of further polymorphs of 1-(4-chlorophenyl)pyrazol-3-ol.

The metal 1-(4-chlorophenyl)pyrazol-3-olate is preferably used in the form of a potassium or sodium salt, wherein potassium is more preferred.

Suitable solvents are anisole or cyclopentyl methyl ether, wherein anisole is preferred.

The aqueous solution of the metal 1-(4-chlorophenyl)pyrazol-3-olate comprises from 5 to 25% by weight of metal 1-(4-chlorophenyl)pyrazol-3-olate, more preferably from 10 to 17% by weight.

The ratio of the metal 1-(4-chlorophenyl)pyrazol-3-olate as aqueous solution to solvent is from 5:1 to 1:5, preferably from 3:1 to 1:3, more preferably from 2:1 to 1:2, for example 1.5:1

The pH of the solution in step a) is adjusted to equal or below 8, preferably adjusted to 2 to 7, more preferably adjusted to 4 to 7, for example adjusted to 6.

The acid can be an inorganic acid or organic acid.

Suitable inorganic acids include hydrohalogenic acids such as hydrochloric and hydrobromic acid, sulfur acids such as sulfuric acid, chlorosulfonic acid, phosphorus acids such as phosphoric acid, and nitrogen acids such as nitric acid, or boron acids such as boric acid. Organic acids, such as formic acid, acetic acid and halogenated acetic acids such as trichloro acetic acid, trifluoro acetic acid, propionic acid, oxalic acid, malonic acid and succinic acid, are also suitable.

Preferred acids are inorganic acids, most preferably hydrochloric acid in various concentrations. The chosen temperature in step a) ranges from 0° C. to the boiling point of the mixture.

In step b) the aqueous phase is removed.

In a further embodiment of the invention, such aqueous phase can be re-extracted with the solvent used in step a). The solvent being used for such extraction can be used for step a).

If the solvent is anisole, temperature ranges from 60° C. to 95° C. are preferred.

If the solvent is cyclopentyl methyl ether, temperature ranges from 50° C. to 90° C. are preferred.

Crystallization in step c) can be achieved by methods known in the art, for example by cooling crystallization, evaporative crystallization or a combination of cooling crystallization and evaporative crystallization.

Cooling crystallization makes use of the fact that the solubility threshold decreases with temperature leading to crystallization of a saturated solution. For example, decreasing the temperature of a solution resulting from step b) leads to crystallization of 1-(4-chlorophenyl)pyrazol-3-ol.

Evaporative crystallization is based on removal of solvent leading to a supersaturated solution, in which crystal formation takes place. Evaporation can be performed usually at elevated temperatures under normal pressure or under reduced pressure. But it is also possible to perform evaporation at ambient temperatures under reduced pressure.

Both processes can be also combined, for example, part of the solvent is removed evaporation at elevated temperatures, wherein the resulting solution is further processed by cooling crystallization.

In both processes, cooling crystallization evaporative crystallization seed crystals can be added.

If seed crystals are added during the crystallization, their amount is typically from 0.001 to 10% by weight, frequently from 0.005 to 5% by weight, in particular from 0.01 to 1% by weight and especially from 0.05 to 0.5% by weight, based on the 1-(4-chlorophenyl)pyrazol-3-ol dissolved.

The resulting crystals are separated from the organic phase by methods known in the art, for example by commonly known filtration methods (such as pressure or vacuum filtration).

Washing of the crystals can be done on the filter by applying the appropriate solvent. In a further embodiment of the invention the resulting wash liquor is recycled and used for step a).

The invention is further illustrated, but not limited by the following examples:

EXAMPLES

Example 1 (with Anisole)

A) Protonation and pH Adjustment:

601.2 g (0.354 mol) of a 13.7% aqueous solution of potassium 1-(4-chlorophenyl)pyrazol-3-olate (pH 13.3) from the production plant is precharged at 22° C. and the agitator is started. 179.2 g (0.492 mol) of HCl (10%) is dosed over 45 min. During addition temperature rises from 22° C. to 27° C. Just after dosage start 1-(4-chlorophenyl)pyrazol-3-ol begins to precipitate. HCl dosage is stopped as soon as a pH of 6 is reached.

B) Extraction:

For extraction, the suspension is heated up to 75° C. and 400.0 g of anisole is added.

The temperature is adjusted to 88° C. to dissolve all precipitates completely. The agitator is stopped and the phases are separated at 88° C.

C) Crystallization, Filtration, Washing, Drying:

For crystallization the agitator is started again and the organic phase is cooled down from 88° C. to −5° C. over 8 h. The suspension is filtered at −5° C. by vacuum filtration. The filter cake is washed with 120.0 g of anisole precooled to −5° C. After drying in a vacuum drying cabinet 62.9 g (90.3%) of dry 1-(4-chlorophenyl)pyrazol-3-ol (98.9% w/w, HPLC with external standard calibration, 275 nm) is obtained.

The X-ray powder diffractogram of 1-(4-chlorophenyl)pyrazol-3-ol at 25° C. (Cu-Kα radiation, 1.54060 Å) shows the following characteristic reflexes [2θ, Cu Kα]: 9.2, 11.2, 12.8, 15.7, 18.4, 19.5, 20.4, 21.3, 23.0, 25.7, 26.7, 27.7

The melting point is determined by DSC [onset]: 180° C. (endothermic), heating rate: 10K/min

Example 2 (with Cyclopentyl Methyl Ether)

A) Protonation and pH Adjustment:

600.3 g (0.348 mol) of a 13.5% aqueous solution of potassium 1-(4-chlorophenyl)pyrazol-3-olate (pH 13.3) from the production plant is precharged at 22° C. and the agitator is started. 176.5 g (0.484 mol) of HCl (10%) is dosed over 44 min. During addition temperature rises from 20° C. to 25° C. Just after dosage start 1-(4-chlorophenyl)pyrazol-3-ol begins to precipitate. HCl dosage is stopped as soon as a pH of 6 is reached.

B) Extraction:

For extraction, 300.0 g cyclopentyl methyl ether is added at 25° C. and the suspension is heated up to 85° C. The agitator is stopped and the phases are separated at 85° C.

C) Crystallization, Filtration, Washing, Drying:

For crystallization the agitator is started again and the organic phase is cooled down from 85° C. to −10° C. over 8 h. The suspension is filtered at −10° C. by vacuum filtration. The filter cake is washed with 100.0 g of cyclopentyl methyl ether pre-cooled to −10° C. After drying in a vacuum drying cabinet 59.1 g (86.7%) of dry 1-(4-chlorophenyl)pyrazol-3-ol (99.4% w/w, HPLC with external standard calibration, 275 nm) is obtained.

The X-ray powder diffractogram of 1-(4-chlorophenyl)pyrazol-3-ol at 25° C. (Cu-Kα radiation, 1.54060 Å) shows the same characteristic reflexes as in example 1.

The melting point is determined by DSC [onset]: 180° C. (endothermic), heating rate: 10K/min

The invention claimed is:

1. A process for preparing crystalline 1-(4-chlorophenyl)pyrazol-3-ol, comprising
    a) contacting an aqueous solution of a metal 1-(4-chlorophenyl)pyrazol-3-olate with a solvent; wherein
        i. the solvent is selected from anisole or cyclopentylmethylether; and
        ii. the temperature is between 0° C. and the boiling point of the mixture; and
        iii. the pH of the mixture is adjusted to ≤8 using an acid; and
    b) removing the aqueous phase; and
    c) crystallizing 1-(4-chlorophenyl)pyrazol-3-ol in the solution resulting from step b).

2. The process of claim 1, wherein the pH of the solution is adjusted to values between 0 and 7.

3. The process of claim 1, wherein the acid is an inorganic acid.

4. The process of claim 1, wherein potassium or sodium 1-(4-chlorophenyl)pyrazol-3-olate is used.

5. The process of claim 1, wherein the solvent is anisole.

6. The process of claim 1, wherein the solvent is cyclopentyl methyl ether.

7. The process of claim 1, wherein crystallization is achieved by cooling crystallization, evaporative crystallization or a combination of cooling crystallization and evaporative crystallization.

* * * * *